United States Patent
Martin et al.

(10) Patent No.: US 9,500,660 B2
(45) Date of Patent: Nov. 22, 2016

(54) ISOVALERYLGLYCINE AS BIOMARKER FOR THE PREDISPOSITON FOR WEIGHT GAIN AND OBESITY

(71) Applicant: Nestec S.A., Vevey (CH)

(72) Inventors: Francois-Pierre Martin, Vuisternens-devant-Romont (CH);
(Continued)

(73) Assignee: Nestec S.A. (CH)

(*) Notice: Subject to any disclaimer, the term of this patent is extended or adjusted under 35 U.S.C. 154(b) by 0 days.

(21) Appl. No.: 14/649,072

(22) PCT Filed: Nov. 25, 2013

(86) PCT No.: PCT/EP2013/074570
§ 371 (c)(1),
(2) Date: Jun. 2, 2015

(87) PCT Pub. No.: WO2014/086605
PCT Pub. Date: Jun. 12, 2014

(65) Prior Publication Data
US 2015/0309051 A1    Oct. 29, 2015

(30) Foreign Application Priority Data

Dec. 4, 2012    (EP) .................................... 12195490

(51) Int. Cl.
G01N 33/50      (2006.01)
G01N 33/68      (2006.01)
(Continued)

(52) U.S. Cl.
CPC .......... *G01N 33/6893* (2013.01); *G01N 24/08* (2013.01); *G01N 33/50* (2013.01);
(Continued)

(58) Field of Classification Search
CPC ............ G01N 2800/60; G01N 2800/70; G01N 33/50; G01N 33/6893; G01N 24/08; C12Q 1/61; C12Q 2565/633
See application file for complete search history.

(56) References Cited

U.S. PATENT DOCUMENTS 5,550,146 A * 8/1996 Acosta .................... A23L 1/296
                                                  514/400
7,993,931 B1 * 8/2011 Chen ...................... G01N 33/50
                                                  436/127
(Continued)

FOREIGN PATENT DOCUMENTS

KR    20110052391 A    5/2011
WO    2004/074482 A1    9/2004
(Continued)

OTHER PUBLICATIONS

Boulange et al, "Early Metabolic Adaptation in c57BL/6 Mice Resistant to High Fat Diet Induced Weight Gain Involves an Activation of Mitochrondial Oxidative Pathways", Journal of Proteome Research, Mar. 8, 2013, pp. 1956-1968.*
(Continued)

*Primary Examiner* — Jennifer Wecker
(74) *Attorney, Agent, or Firm* — Kevin C. Hooper

(57) ABSTRACT

The present invention relates generally to the field of nutrition and health. In particular, the present invention relates to a new biomarker, its use and a method that allows it to diagnose the likelihood to resist diet induced weight gain, and/or to be susceptible to a diet induced weight gain. For example, the biomarker may be isovalerylglycine.

16 Claims, 9 Drawing Sheets

Figure 1:
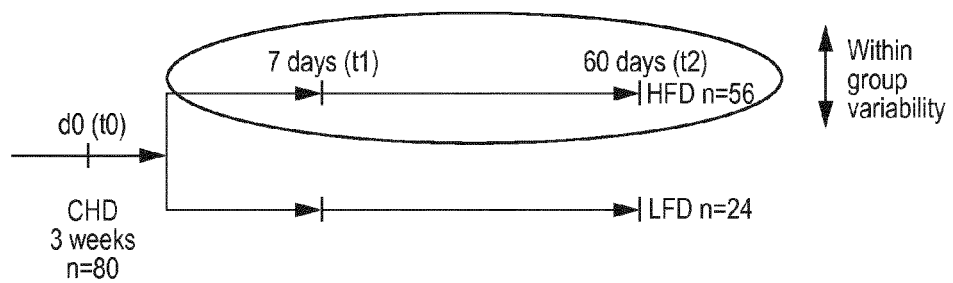
Figure 1:
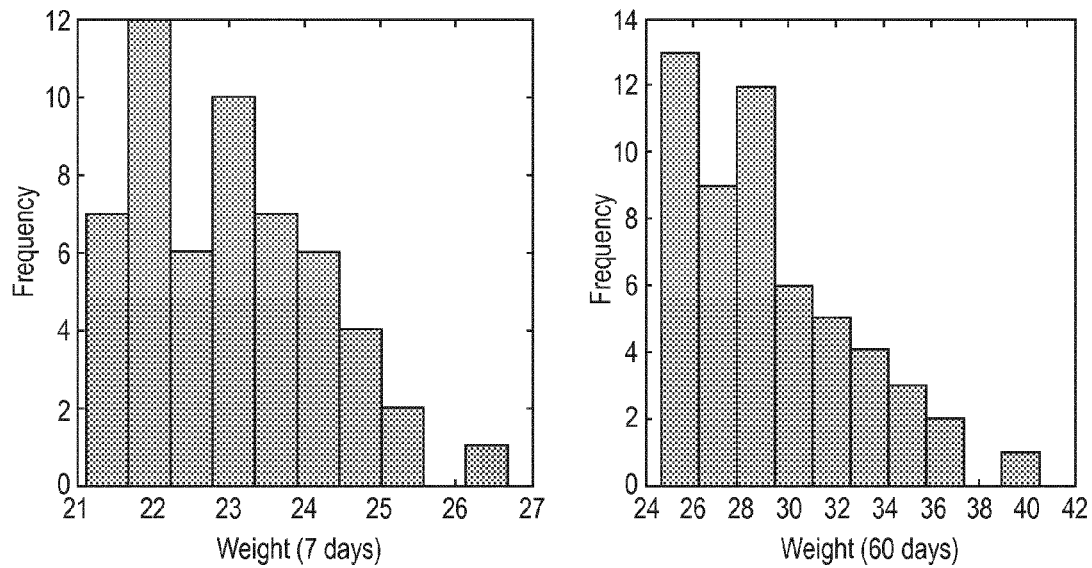
Figure 1:
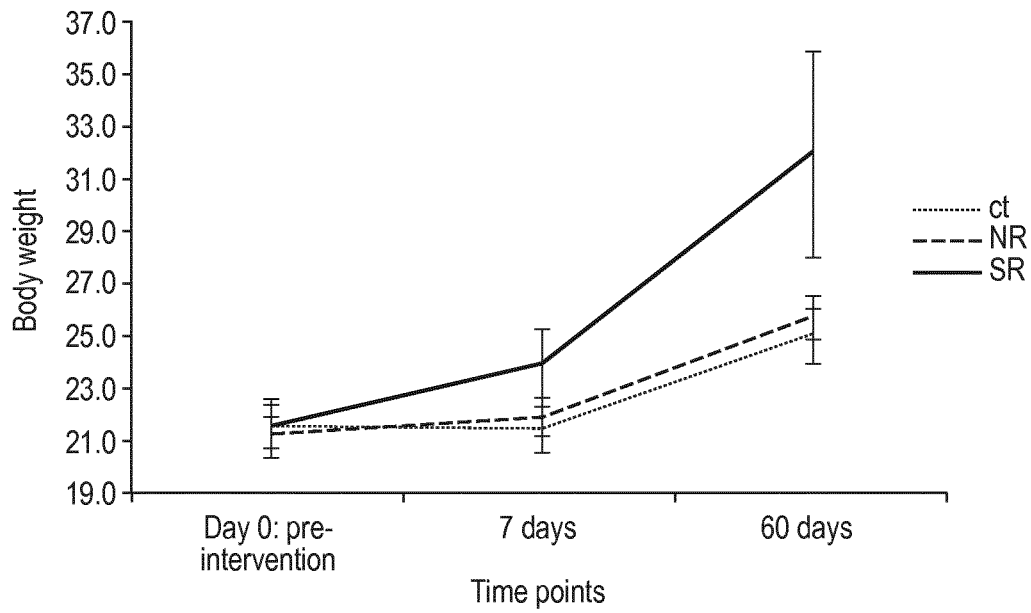
Figure 1:
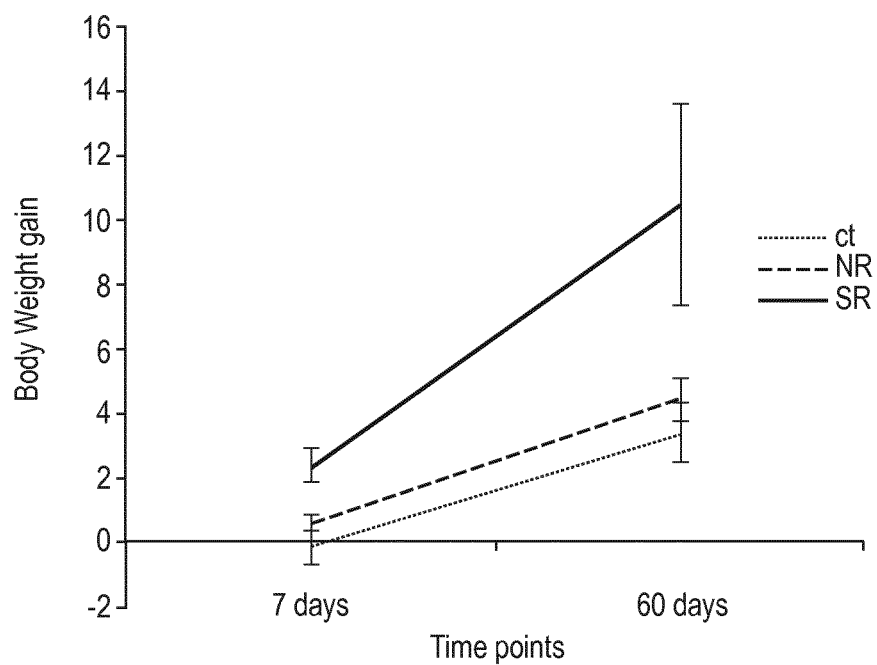

(72) Inventors: Claire L. Boulange, London (GB);
Ivan Montoliu Rora, Lausanne (CH);
Sebastiano Collino, Lausanne (CH);
Marc-Emmanuel Dumas, London (GB); Elaine Holmes, Croydon (GB);
Serge Andre Dominique Rezzi, Semsales (CH); Jeremy Nicholson, Croydon (GB); Sunil Kochhar, Savigny (CH)

(51) Int. Cl.
*G01N 24/08* (2006.01)
*A61B 5/00* (2006.01)
*H01J 49/00* (2006.01)
*C12Q 1/61* (2006.01)

(52) U.S. Cl.
CPC ........... *C12Q 1/61* (2013.01); *C12Q 2565/633* (2013.01); *G01N 2800/044* (2013.01); *G01N 2800/50* (2013.01); *G01N 2800/60* (2013.01); *G01N 2800/70* (2013.01)

(56) References Cited

U.S. PATENT DOCUMENTS

| | | | |
|---|---|---|---|
| 2006/0160237 A1* | 7/2006 | Du | G01N 30/8675 436/129 |
| 2007/0043518 A1* | 2/2007 | Nicholson | G06F 19/703 702/23 |
| 2009/0318556 A1 | 12/2009 | Idle et al. | |

FOREIGN PATENT DOCUMENTS

| | | |
|---|---|---|
| WO | 2010/138899 | 12/2010 |
| WO | 2014/086603 | 6/2014 |
| WO | 2014/086604 | 6/2014 |

OTHER PUBLICATIONS

Jung et al, "1 H NMR-based metabolite profiling of diet-induced obesity in a mouse mode", BMB reports by the Korean Society for Biochemistry and Molecular Biology, Dec. 2011, pp. 419-424.*

Newgard, et al., "A branched-chain amino acid-related metabolic signature that differentiates obese and lean human and contributes to insulin resistance", Cell Metabolism, 9, Apr. 2009, pp. 311-326.*

Kimura, et al., "Screening for fatty acid beat oxidation disorders acylglycine analysis by electron impact ionization gas chromatography-max spectrometry", Journal of Chromatography B, 731, 1999, pp. 105-110.*

Tomlinson et al., "Cannabinoid receptor antagonist-induced striated muscle toxicity and ethylmalonic-adipic aciduria in beagle dogs", Toxicological Sciences 192(2), 2012, pp. 268-279.

Boulange', et al., "Early metabolic adaptation in C57BL/6 mice resistant to high fat diet induced weight gain involved an activation of mitochondrial oxidative pathways", Journal of Proteome Research, 2013, p. 1956.

International Search Report for PCT/EP2013/074570 dated Feb. 24, 2014.

Dean, et al., "Glycine supplementation to low protein, amino acid-supplemented diets supports optimal performance of broiler chicks", Poultry Science 2006, 85 pp. 288-296.

Gu, et al., "1H NMR metabolomics study of age profiling in children", NMR in Biomedicine, 2009, 22, pp. 826-833.

Kim et al., "1H NMR-based metabolomic study on resistance to diet-induced obesity in AHAK knock-out mice", Biochemical and Biophysical Research Communications 403, 2010, pp. 428-434.

Stella, et al., "Susceptibility of human metabolic phenotypes to dietary modulation", Journal of Proteome Research, 2006, 5; pp. 2780-2788.

Lloyd, et al., "Use of Mass spectrometry fingerprinting to identify urinary metabolites after consumption to specific foods", Am. J. Clin. Nutr. 2011: 94: pp. 981-991.

Zhen, et al., "Metabolomic and genetic analysis of biomarkers for peroxisome proliferator-activated receptor α expression and activation", Molecular Endocrinology 21(9), 2007 pp. 2136-2151.

International Search Report for PCT/EP2013/074566 dated Feb. 3, 2014.

International Search Report for PCT/EP2013/074567 dated Jan. 31, 2014.

Non-Final Office Action for U.S. Appl. No. 14/649,055 dated Nov. 18, 2015.

* cited by examiner

ISOVALERYLGLYCINE AS BIOMARKER FOR THE PREDISPOSITON FOR WEIGHT GAIN AND OBESITY

The present invention relates generally to the field of nutrition and health. In particular, the present invention relates to a new biomarker, its use and a method that allows it to diagnose the likelihood to resist diet induced weight gain, and/or to be susceptible to a diet induced weight gain. For example, the biomarker may be isovalerylglycine. This biomarker may also be used for diagnosing/monitoring the effect of a change in lifestyle on weight gain risk in a subject.

Obesity has become one of the most important global healthcare problems in the 21st century as it raises the risk to develop further diseases including type 2 diabetes, hepatic steatosis (NAFLD), cancers, arthritis and cardiovascular diseases (CVD). The aetiology of obesity results from a complex interaction between genetic and environmental factors such as high caloric diet, lack of physical activity and behaviour. Gut microbiota being involved in various physiological functions such as the maturation of gut's innate immune system and the digestion/absorption of nutrients also influences the development of several metabolic diseases and seem to have a significant impact on obesity. Hence, individual predisposition of developing obesity varies according to these multi-factorials causes.

Ingestion of an unbalanced diet rich in fat and/or carbohydrate has been associated with an increased rate of triglyceride storage in adipose tissues as well as lean tissues such as liver, muscle and heart. This ectopic fat deposition inducing lipotoxicity is also correlated with a range of metabolic disorders such as hypertriglyceridemia, hypertension, high fasting glucose and insulin resistance (IR). Nonetheless, some overweight or obese people may develop various metabolic disorders and while others stay healthy. For instance, the localisation of fat deposition in the body influences the development of metabolic disorders. Epicardial fat, being efficient to release proatherogenic adiponectines and process fatty acids, has been positively correlated with CVD markers in humans. By contrast, intra-hepatic fat has been associated with inflammation and insulin resistance. Wildman et al. also highlighted that race-ethnic differences in healthy middle age women are associated with differential metabolic activity of visceral and subcutaneous adipose tissues which could influence the ethnic-related predisposition to develop obesity and CVD]. As a result, it is relevant to identify the likelihood to develop obesity-related metabolic disorders at an early stage, in order to assess the individual metabolic status and to effectively prevent the development of metabolic diseases.

It would therefore be desirable to provide the art with a method that allows it to identify subjects early—ideally before they put on weight—that are likely gain weight when consuming diets rich in fats.

Any reference to prior art documents in this specification is not to be considered an admission that such prior art is widely known or forms part of the common general knowledge in the field.

The object of the present invention is to improve the state of the art and in particular to provide a method that allows it to effectively stratify people early whether or not they are likely to respond to a high fat diet with weight gain.

The inventors were surprised to see that the object of the present invention could be achieved by the subject matter of the independent claims. The dependent claims further develop the idea of the present invention.

Accordingly, the present invention provides a biomarker, its use and a method for diagnosing the likelihood to resist a high fat diet induced weight gain.

As used in this specification, the words "comprises", "comprising", and similar words, are not to be interpreted in an exclusive or exhaustive sense. In other words, they are intended to mean "including, but not limited to".

The inventors have used a metabonomics approach to achieve the objective of the present invention. Metabonomics is considered today a well-established system approach to characterize the metabolic phenotype, which comprises the influence of various factors such as environment, drugs, diet, lifestyle, genetics, and microbiome factors. Unlike gene expression and proteomic data that indicate the potential for physiological changes, metabolites and their dynamic concentration changes within cells, tissues and organs, represent the real end-points of physiological regulatory processes.

It is therefore a suitable approach to investigate the gradual metabolic changes linked to various dietary interventions and diseases development. Recently, metabolomics and lipidomics-based discoveries have been accelerating our understanding of disease processes, and will provide novel avenues for prevention and nutritional management of the sub-clinical disorders associated to metabolic syndrome. In particular, "omics" data have highlighted the contribution of energy metabolism (Krebs's cycle), lipid and amino acid processing, as well as inflammatory signals to the onset of obesity and insulin resistance (IR).

Using a combination of proton nuclear magnetic resonance ($^1$H NMR) spectroscopy of urine samples collected overtime and weight gain monitoring, the inventors have identified novel metabolic biomarkers of gradual weight gain induced by a high fat diet in a well defined C57BL/6 mouse model. This animal model is well known to show extreme phenotypes across isogenic animals, i.e. animals resistant or prone to high fat induced weight gain distribution. The present inventors have characterised the short term (7 day) and long term (60 day) metabolic adaptation of C57BL/6 mice fed with a high fat diet (HFD) and have established the specific metabolic signatures associated with phenotype variability within HFD fed mice, i.e. animals resistant or prone to high fat induced weight gain. By using a metabonomic approach, the inventors have showed that mitochondrial metabolic pathways (fatty acid β oxidation, branched-chain amino acid catabolism, butanoate metabolism, nicotinamide adenine dinucleotide pathway and Krebs's cycle) are quickly up-regulated by high fat feeding which might reflect a fatty acid saturation of mitochondria and an impairment of energy metabolism.

The inventors could show that obesity resistant mice under HFD are associated with a specific activation of mitochondrial oxidative pathways (β oxidation, butanoate metabolism and leucine catabolism) which may be a protective mechanism against fatty acid overloading.

These results emphasize the role of mitochondria in obesity development and allows the conclusion that the likelihood to develop metabolic disorders, such as obesity, can be determined from an early metabolic signature using a specific set of biomarkers that the inventors have identified.

The inventors were able to show that the urine metabolic response after one week on high fat feeding (Day 7) enables not only the prediction of the final weight gain for each individual (Day 60), but also to stratify animals according to their predisposition to be resistant or prone to high fat induced weight gain.

Consequently, the present invention relates to a novel biomarker, isovalerylglycine.

The invention further relates to the use of isovalerylglycine as a biomarker in urine for detecting and/or quantifying the likelihood to resist high fat diet induced weight gain.

Similarly, the invention also relates to the use of isovalerylglycine as a biomarker in urine for detecting and/or quantifying the likelihood to be susceptible to high fat diet induced weight gain.

The invention also relates to a method of diagnosing the likelihood to resist high fat diet induced weight gain in a subject, comprising determining the level of isovalerylglycine in a urine sample previously obtained from a subject to be tested, and comparing the subject's isovalerylglycine level to a predetermined reference value, wherein the predetermined reference value is based on an average isovalerylglycine level in urine in a control population, and wherein an increased isovalerylglycine level in the sample compared to the predetermined reference value indicates an increased likelihood to resist high fat diet induced weight gain. Similarly, the invention also relates to a method of diagnosing the likelihood be susceptible to high fat diet induced weight gain in a subject, comprising determining the level of isovalerylglycine in a urine sample previously obtained from a subject to be tested, and comparing the subject's isovalerylglycine level to a predetermined reference value, wherein the predetermined reference value is based on an average isovalerylglycine level in urine in a control population, and wherein a decreased isovalerylglycine level or the absence of change in the sample compared to the predetermined reference value indicates a increased likelihood to be susceptible to high fat diet induced weight gain.

This biomarker of the present invention may also be used for diagnosing and/or monitoring the effect of a change in lifestyle on weight gain risk in a subject. For this the biomarker level may be assessed before the lifestyle change and the resulting level may be compared to the level of the said biomarker after the lifestyle change.

FIG. 1: Variability of body weight gain in a population of n=56 mice fed a HFD. (A) Experimental design. (B) Body weight distribution of mice after 7 days and 60 days of HFD feeding. (C) Identification of non-responder (NR) and strong responder (SR) mice to obesity at each time-point. Several NR and SR mice are observed in 2 time points or during the overall course of the experiment. (D) Weight monitoring of control (n=24), NR (n=30), and SR (n=29) mice before the diet (t0), after 7 days (t1) and 60 days (t2), of HFD feeding. s(n=average±standard error, p value for non parametric Mann and Whitney test *<0.05, <0.001, *<0.0001.)

Figure 2:
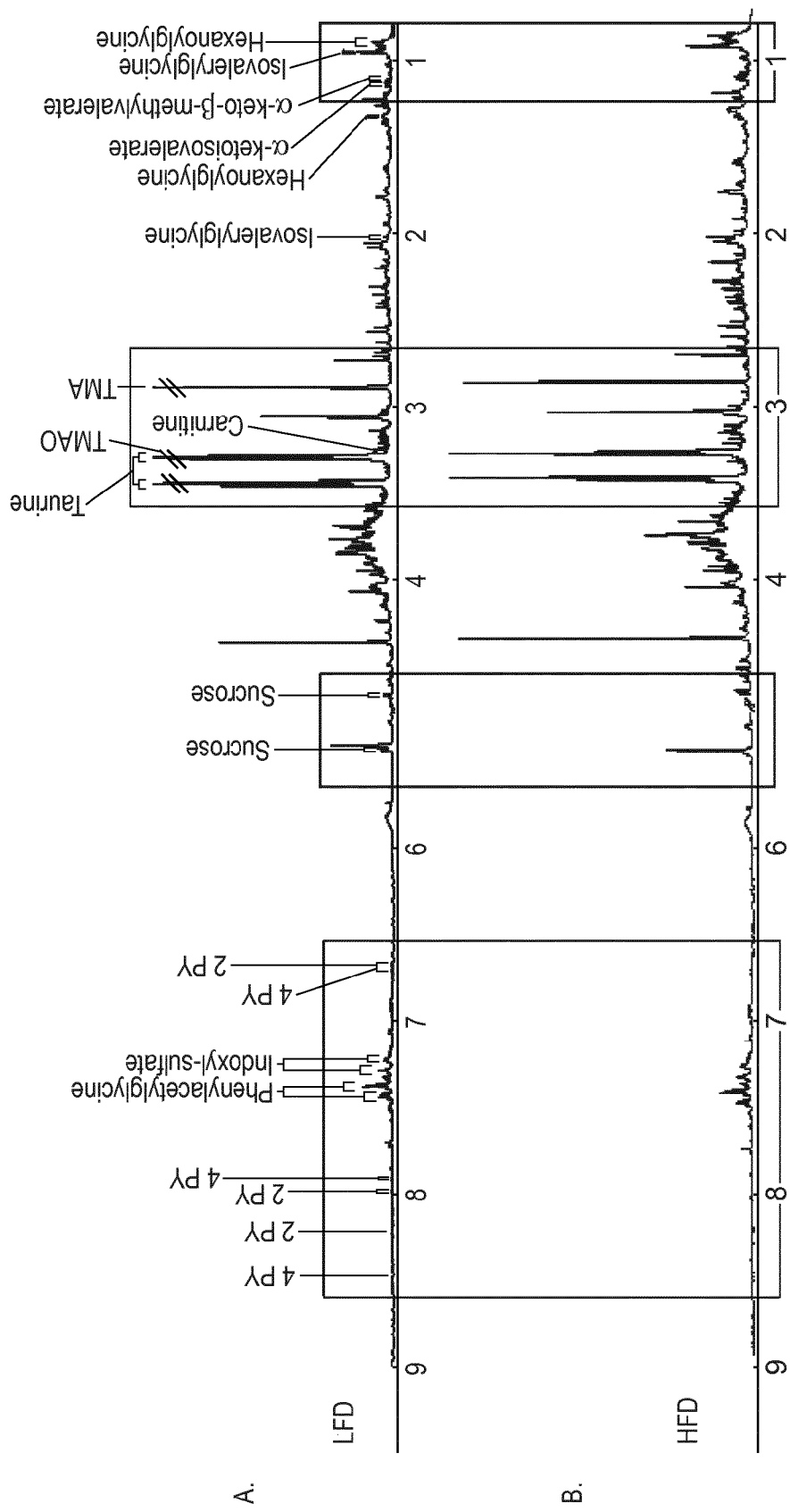
Figure 2:
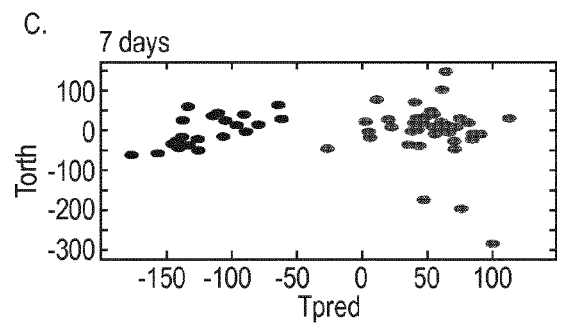
Figure 2:
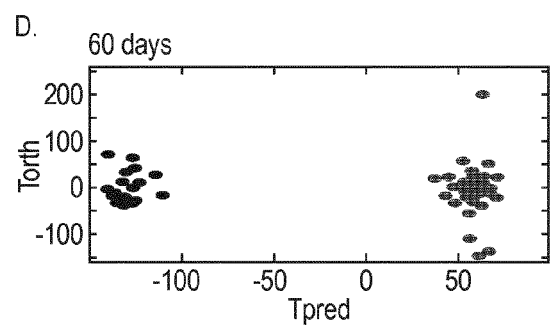
Figure 2:
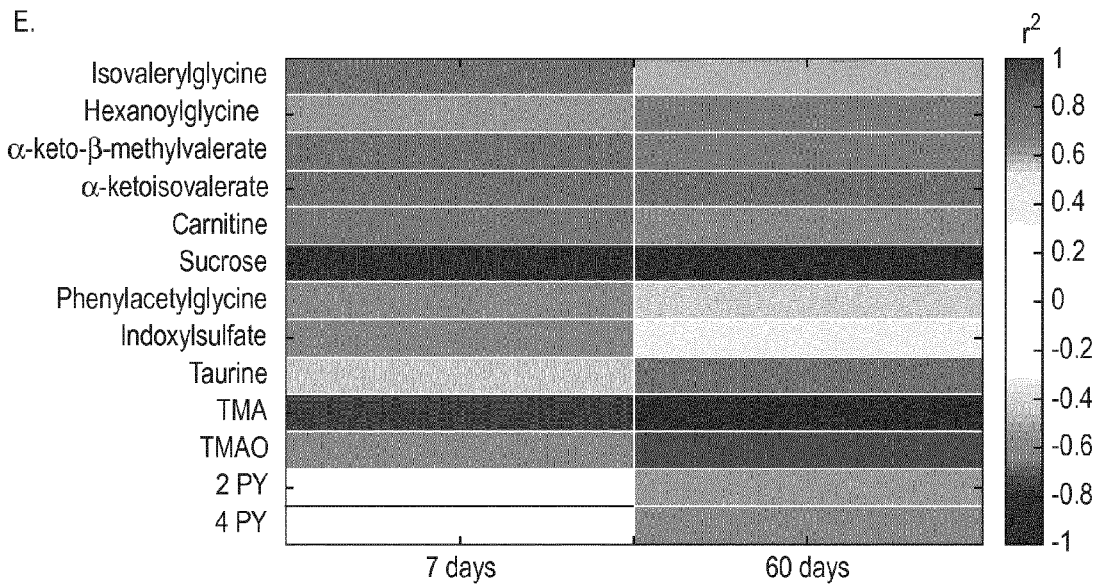

FIG. 2: $^1$H NMR urine metabolic profile of C57BL/6 HFD fed or LFD fed mice 7 days and 60 days after the diet switch. (A) Mean $^1$H NMR spectrum of urine from LFD fed mice or (B) HFD fed mice. (C) OPLS-DA score plot of urine metabolic profile of LFD and HFD fed mice at 7 days (D) OPLS-DA score plot of urine metabolic profile of LFD and HFD fed mice at 60 days. (E) Heatmap obtained from the OPLS-DA coefficient plots showed metabolites found to be significantly different in HFD and LFD fed mice. Correlation values of the metabolites are displayed by color code. (Gradient of red color for metabolites positively correlated with HFD-fed mice and gradient of blue colors for metabolites negatively correlated).

Figure 3:
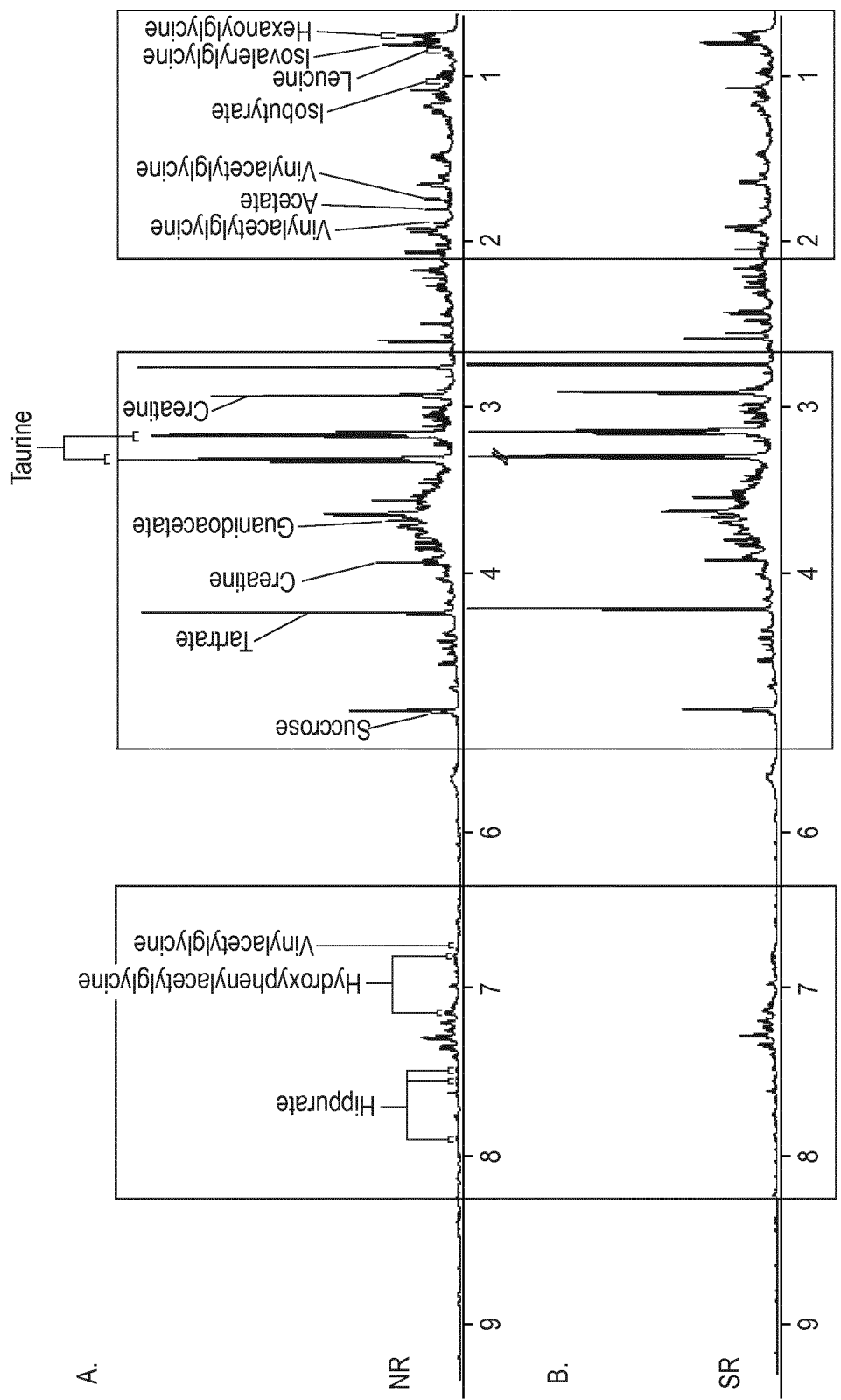
Figure 3:
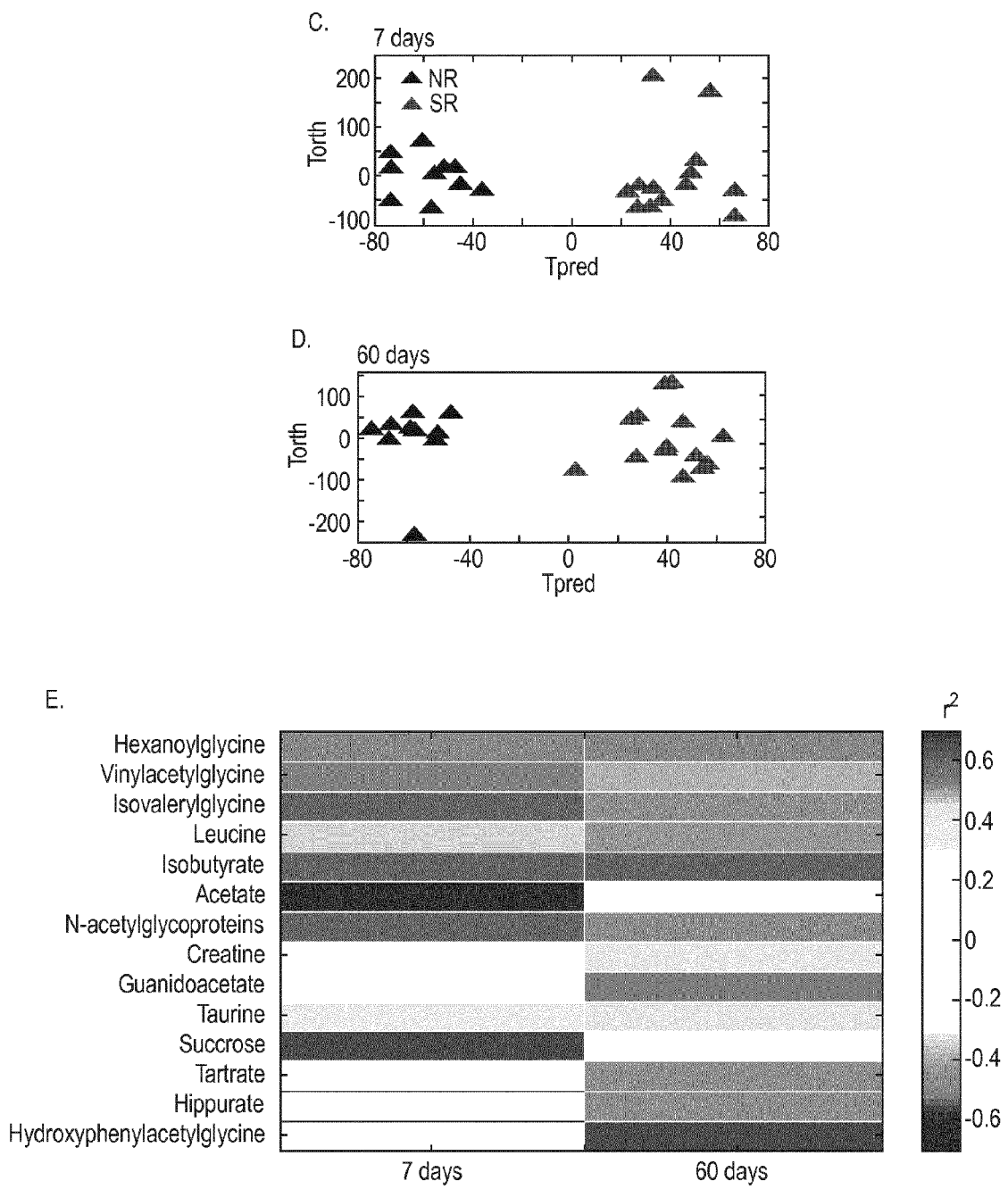

FIG. 3: Specific metabolic signature of NR and SR mice. (A) Mean of $^1$H NMR spectra of urine from NR mice or (B) SR mice. (C) OPLS-DA score plot of urine metabolic profile of NR and SR mice at 7 days (D) and 60 days. (E) Heatmap obtained from the OPLS-DA coefficient plots showed metabolites found to be significantly different in NR and SR mice. Correlation values of the metabolites are displayed by color code. (Gradient of red color for metabolites positively correlated with SR mice and gradient of blue colors for metabolites negatively correlated).

Figure 4:
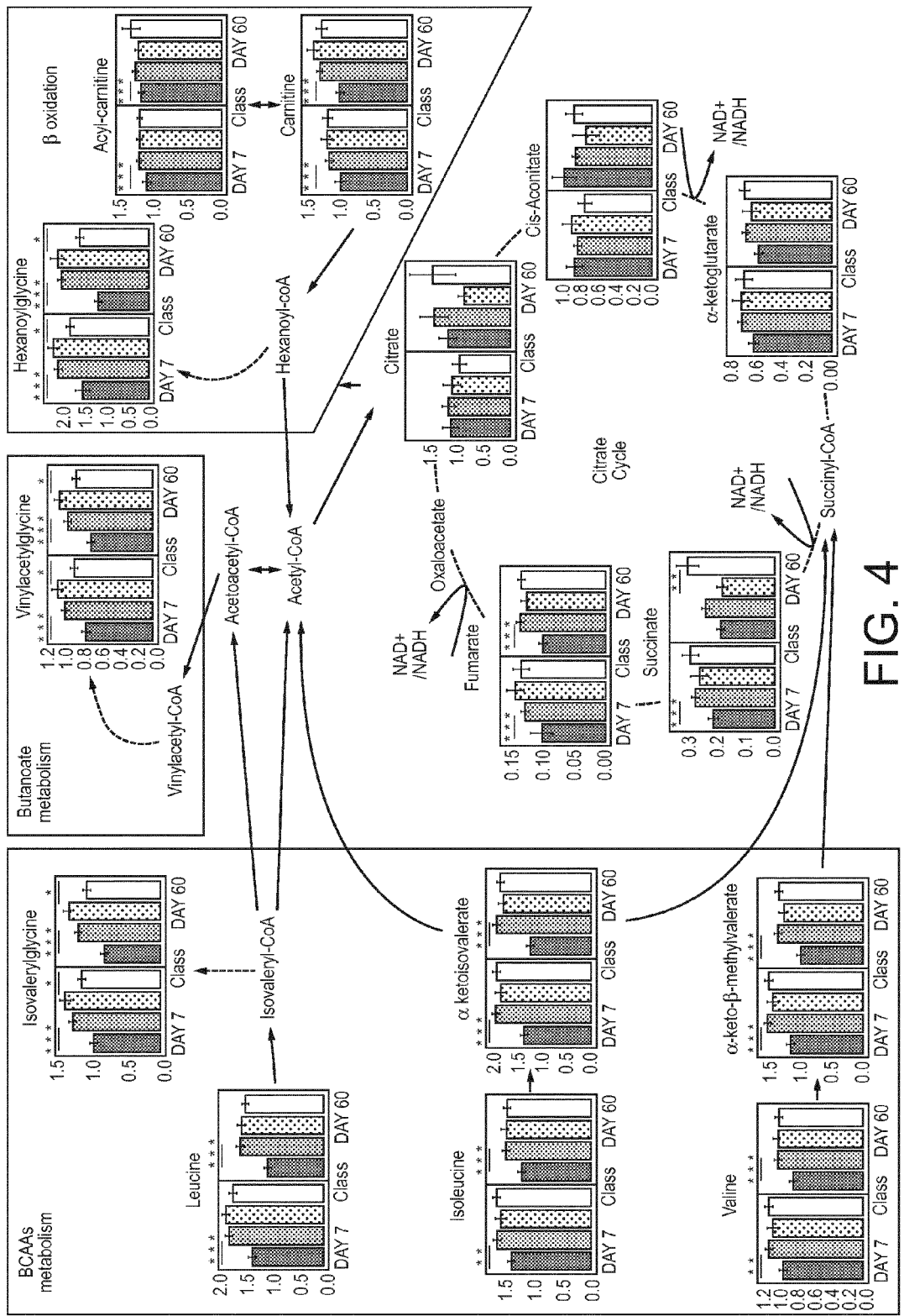
Figure 4:
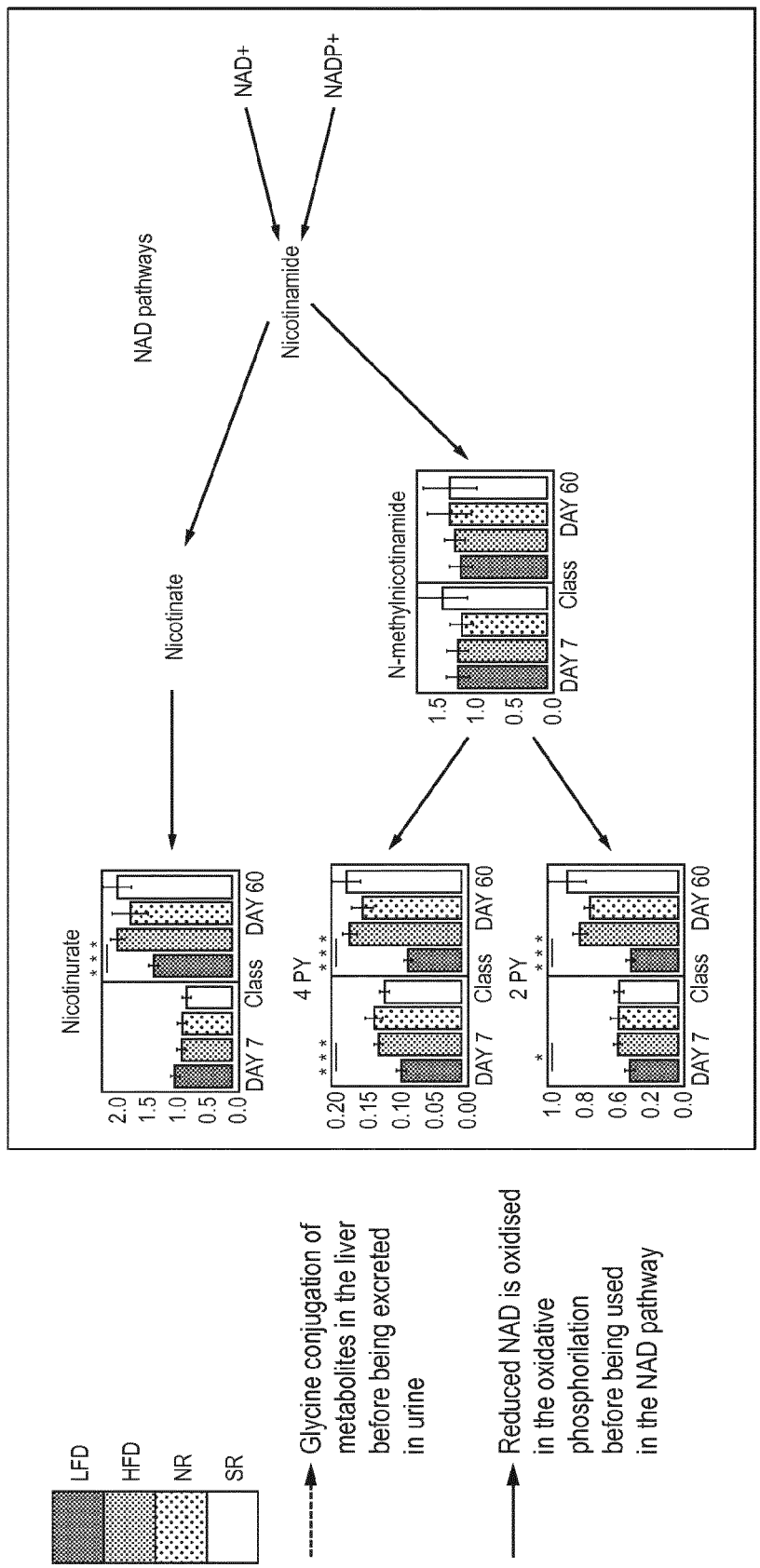

FIG. 4: Mapping of the urinary excretion pattern of metabolites involved in BCAAs, butanoate, Nicotinamide adenine dinucleotide metabolism, Krebs's cycle and β oxidation. The bar plots showed the mean ratio with standard error of metabolite integrals at day 7 to day 0 or day 60 to day 0. The Y axis indicates the value of the mean for LF, HF, NR and SR mice (arbitrary unit). Significant difference between mean ratios of LF and HF or NR and SR were calculated with non parametric Mann Whitney test: *<0.05, <0.001, *<0.0001 (values of mean, standard errors and p value in supplementary tables 3 and 4). Indirect metabolic reactions are highlighted with dash arrows.

Figure 5:
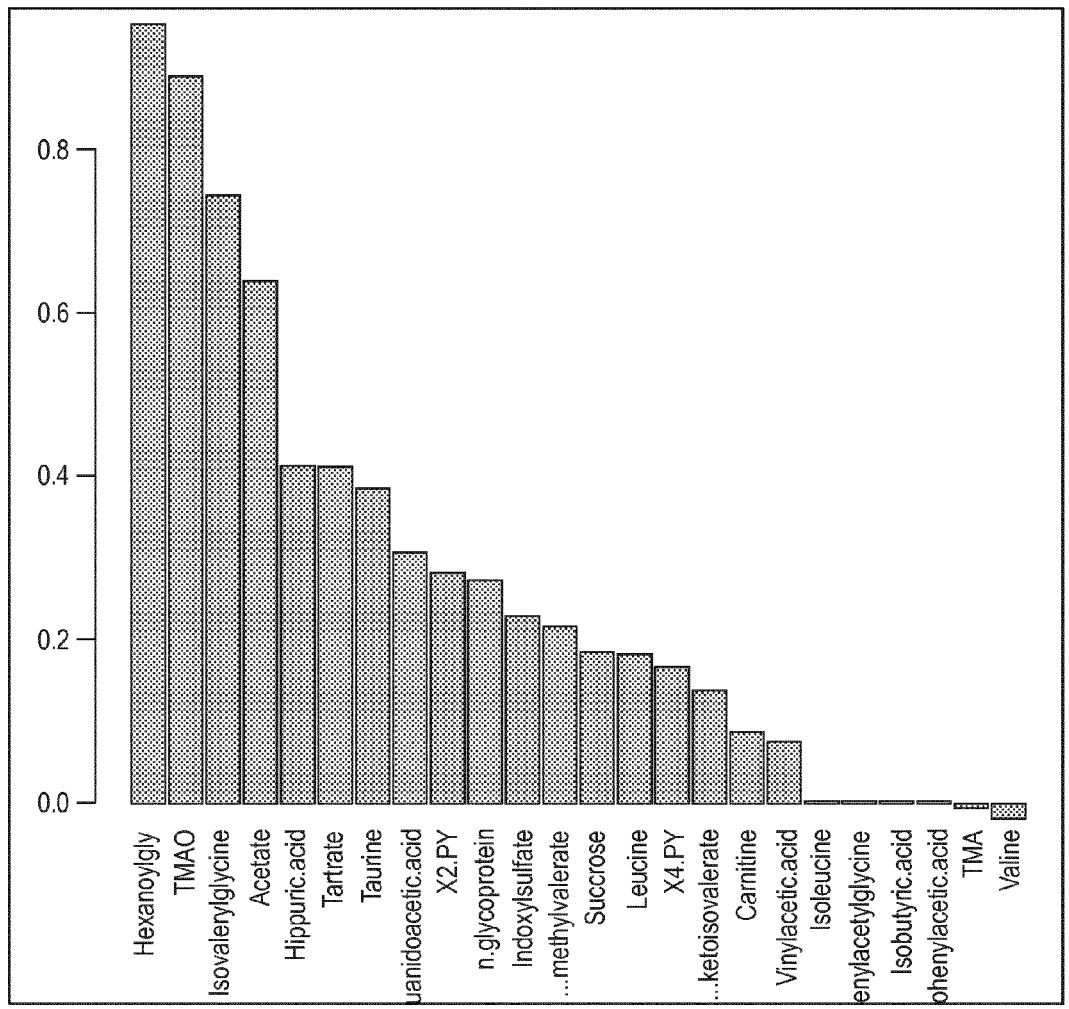

FIG. 5 shows metabolite importance and robustness in predicting NR and SR as assessed by Random forest analysis.

Table 1: Summary of relationships between metabolites and weight gain in high fat induced weight gain Table 2: Summary of the fold of changes in selected metabolites over time in weight gain resistant (NR) and prone (SR) individuals The present invention relates in part to a biomarker, wherein the biomarker is isovalerylglycine.

In the experiments described herein, mice fed with a HFD displayed a urinary increase of isovalerylglycine over time. Without wishing to be bound by theory, the inventors currently believe that the increase of several Krebs's cycle intermediates and end-products of nicotinamide adenine dinucleotide pathways in urine of HFD mice may be considered evidence for energy over-production in mitochondria. The chronic increase of mitochondria oxidative pathways are considered to be deleterious for the mitochondria leading to impairment of oxidative pathways and of energy metabolism. In addition, the excess of free fatty acids can be stored as triglycerides in adipose tissues as well as in lean tissues which may promote organ dysfunction and metabolic diseases such as hepatic steatosis or cardiovascular diseases.

The inventors have found that isovalerylglycine may be used as a biomarker in a body fluid for detecting and/or quantifying the likelihood to resist high fat diet induced weight gain. The body fluid may be urine. Using urine as body fluid has the advantage that it can be obtained regularly, non-invasively and without the support of medical personnel.

This diagnostic method is practiced outside of the human or animal body. Typically, the biomarker detection and/or quantification step is carried out in a body fluid sample that was previously obtained from the subject to be tested.

While the present invention is described in view of quantifying the likelihood to resist high fat diet induced weight gain, it is clear to skilled artesians that the same method can be also used for quantifying the likelihood to be susceptible to a high fat diet induced weight gain. Skilled artesians understand that if an increased level of a biomarker is indicative for an increased likelihood to resist high fat diet induced weight gain, a decreased level of a biomarker is indicative for an increased likelihood to be susceptible to a high fat diet induced weight gain, and vice versa.

Hence the present invention also related to the use of isovalerylglycine as a biomarker in urine for detecting and/or quantifying the likelihood to be susceptible to high fat diet induced weight gain.

The present invention also relates to a method of diagnosing the likelihood of a subject to resist high fat diet induced weight gain, comprising determining the level of isovalerylglycine in a urine sample previously obtained from a subject to be tested, and comparing the subject's isovalerylglycine level to a predetermined reference value, wherein the predetermined reference value is based on an average isovalerylglycine level in urine in a control population, and wherein an increased isovalerylglycine level in the sample compared to the predetermined reference value indicates an increased likelihood to resist high fat diet induced weight gain.

The present invention also relates to a method of diagnosing the likelihood of a subject to be susceptible to high fat diet induced weight gain, comprising determining the level of isovalerylglycine in a urine sample previously obtained from a subject to be tested, and comparing the subject's isovalerylglycine level to a predetermined reference value, wherein the predetermined reference value is based on an average isovalerylglycine level in urine in a control population, and wherein a decreased isovalerylglycine level in the sample compared to the predetermined reference value indicates an increased likelihood to be susceptible to high fat diet induced weight gain.

Using urine as sample has the advantage that in can be obtained non-invasively using a well established procedure. The actual diagnosis method is then carried out outside the body.

The level of isovalerylglycine in the sample can be detected and quantified by any means known in the art. For example, $^1$H-NMR, mass spectroscopy, e.g, UPLC-ESI-MS/MS, may be used. Other methods, such as other spectroscopic methods, chromatographic methods, labeling techniques, or quantitative chemical methods may be used as well. Ideally, the isovalerylglycine level in the sample and the reference value are determined by the same method.

The predetermined reference value may be based on an average isovalerylglycine level in the tested body fluid in a control population. The control population can be a group of at least 3, preferably at least 10, more preferred at least 50 people with a similar genetic background, age and average health status.

The present invention allows it, for example, to stratify subjects early, before they put on weight which may result in health risks. By being aware whether one is susceptible to high fat diet induced weight gain, one can adjust lifestyle and diet accordingly early. An appropriate lifestyle, ideally accompanied by a personalized nutritional regime allows it to maintain a healthy physique and avoids that one has to make significant efforts in terms of caloric restrictions and/or exercise regimens to regain that healthy physique.

While isovalerylglycine as sole marker is effective as a tool for the diagnosis method of the present invention, the quality and/or the predictive power of said diagnosis will be improved, if the diagnosis relies on more than just one marker.

Hence one or more other markers for diagnosing an increased likelihood to resist high fat diet induced weight gain and/or for diagnosing an increased likelihood to be susceptible to high fat diet induced weight gain may be used in combination with isovalerylglycine.

The inventors were surprised to see that also other biomarkers can be used to detect an increased likelihood to resist high fat diet induced weight gain and/or for diagnosing an increased likelihood to be susceptible to high fat diet induced weight gain.

As such the inventors have identified that increased urine concentrations of hexanoylglycine, leucine, isobutyrate, acetate, and decreased urine concentrations of trimethylamine-N-oxide, guanidoacetate, sucrose, tartaric acid, hippuric acid and hydroxyphenylacetylglycine allow diagnosing an increased likelihood to resist high fat diet induced weight gain.

The methods of the present invention may, hence, further comprise the steps of determining the level of at least one further biomarker selected from the group consisting of hexanoylglycine, trimethylamine-N-oxide, leucine, isobutyrate, acetate, guanidoacetate, sucrose, tartaric acid, hippuric acid and hydroxyphenylacetylglycine in the urine sample, and comparing the subject's level of the at least one further biomarker to a predetermined reference value, wherein the predetermined reference value is based on average levels of that at least one further biomarker in a urine sample of a normal healthy control population, and wherein an increased hexanoylglycine, leucine, isobutyrate, acetate, and a decreased trimethylamine-N-oxide, guanidoacetate, sucrose, tartaric acid, hippuric acid and/or hydroxyphenylacetylglycine level in the urine sample compared to the predetermined reference values indicates an increased likelihood to resist high fat diet induced weight gain. Accordingly, a decreased hexanoylglycine, leucine, isobutyrate, acetate, and an increased trimethylamine-N-oxide, guanidoacetate, sucrose, tartaric acid, hippuric acid and/or hydroxyphenylacetylglycine level in the urine sample compared to the predetermined reference values indicates an increased likelihood to be susceptible to high fat diet induced weight gain.

Also the further biomarkers may be detected and quantified by $^1$H-NMR or mass spectroscopy, e.g, UPLC-ESI-MS/MS. Other methods, such as other spectroscopic methods, chromatographic methods, labeling techniques, or quantitative chemical methods may be used as well.

Ideally, all assessed biomarkers are assessed by the same technology. They may be assessed simultaneously.

For example, isovalerylglycine may be assessed together with trimethylamine-N-oxide.

Isovalerylglycine may also be assessed together with hexanoylglycine.

Isovalerylglycine may also be assessed together with leucine.

Isovalerylglycine may also be assessed together with acetate.

Isovalerylglycine may also be assessed together with trimethylamine-N-oxide and hexanoylglycine.

Isovalerylglycine may also be assessed together with trimethylamine-N-oxide, hexanoylglycine, and leucine.

Isovalerylglycine may also be assessed together with trimethylamine-N-oxide, hexanoylglycine, and acetate.

Isovalerylglycine may also be assessed together with trimethylamine-N-oxide, hexanoylglycine, acetate, and leucine.

Isovalerylglycine may also be assessed together with trimethylamine-N-oxide, hexanoylglycine, acetate, leucine, and guanidoacetate.

Isovalerylglycine may also be assessed together with trimethylamine-N-oxide, hexanoylglycine, acetate, leucine, guanidoacetate and hippuric acid.

The advantage of assessing more than one biomarker is that the more biomarkers are evaluated the more reliable the diagnosis will become. If, e.g., more than 1, 2, 3, 4, 5, 6, or 7 biomarkers exhibit the elevations or decreases in concentration as described above, the predictive power for detecting and/or quantifying the likelihood to resist and/or be susceptible to high fat diet induced weight gain is stronger.

The reference value for isovalerylglycine and optionally for the other biomarkers is preferably measured using the same units used to characterize the level of isovalerylglycine and optionally the other biomarkers obtained from the test subject. Thus, if the level of the isovalerylglycine and optionally the other biomarkers is an absolute value such as the units of isovalerylglycine in µmol/l (µM) the reference value is also based upon the units of isovalerylglycine in µmol/l (µM) in individuals in the general population or a selected control population of subjects.

Moreover, the reference value can be a single cut-off value, such as a median or mean. Reference values of isovalerylglycine and optionally the other biomarkers in obtained body fluid samples, such as mean levels, median levels, or "cut-off" levels, may be established by assaying a large sample of individuals in the general population or the selected population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is incorporated herein by reference.

Skilled artesians will know how to assign correct reference values as they will vary with gender, race, genetic heritage, health status or age, for example.

In the method of the present invention, a decreased likelihood to resist high fat diet induced weight gain is indicative for the likelihood to develop disorders associated with overweight and/or obesity.

"Overweight" is defined for an adult human as having a BMI between 25 and 30. "Body mass index" or "BMI" means the ratio of weight in kg divided by the height in meters, squared. "Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

Disorders associated with overweight and/or obesity may be cardio metabolic diseases and/or metabolic deregulations.

The method of the present invention allows it for example to determine the degree of susceptibility of subjects to diet induced weight gain. The method may hence allow stratifying patients according to their likelihood to put on weight based on a high caloric—in particular high fat—diet, independently from whether they are presently underweight, normal, overweight or obese. Adult people are considered underweight if they have a BMI equal to or less than 18.5.

The method of the present invention may also be carried out in underweight, normal, overweight or in obese subjects. In particular in underweight, overweight or in obese subjects the method of the present invention may help to elucidate the genetic predisposition of the subject. Based thereon—and ideally under further consideration of their general health status and lifestyle—personalized nutritional regimens may be developed, that can help to maintain or regain a healthy status.

The method of the present invention is not limited to humans. It may also be used in animals, such as companion animals, for example. Companion animals, such as cats or dogs may be analyzed. Based thereon nutritional regimens may be designed that will contribute to a long life of the companion animal in good health.

The study presented in this application provides insight in the physiological mechanisms related to HF (high fat) induced obesity development and particularly highlights the specific metabolic adaptations associated to obese phenotype variability. High fat ingestion provokes a rapid and consistent up-regulation of mitochondrial metabolic pathways resulting in more production of energy and increased mitochondrial fatty acid saturation. Among the HF fed mice, obesity-resistant (NR) mice were identified, which particularly activated specific mitochondrial metabolic pathways ($\beta$ oxidation, butanoate metabolism and leucine catabolism) and seemed to maintain energy homeostasis (activity of Krebs's cycle comparable to LFD). The inventor's results hence suggest that a specific activation of mitochondrial oxidative pathways might enable to conserve energy homeostasis and protect mitochondria against fuel overloading. Therefore, the role of mitochondria seems to be crucial in the development of obesity and its associated metabolic disorders. Consequently, this comprehensive analysis of the mechanisms underlying heterogeneous adaptation to HFD feeding provides novel and promising perspectives for weight management programs and personalized nutritional solutions.

Hence, if the method of the present invention allows identifying a decreased likelihood to resist high fat diet induced weight gain—or an increased likelihood to be susceptible to high fat diet induced weight gain—this may be indicative for a lack of specific activation of mitochondrial oxidative pathways.

Conversely, if the method of the present invention allows identifying an increased likelihood to resist high fat diet induced weight gain—or a decreased likelihood to be susceptible to high fat diet induced weight gain—this may be indicative for a specific activation of mitochondrial oxidative pathways.

The mitochondrial oxidative pathways may be selected from the group consisting of $\beta$ oxidation, butanoate metabolism and leucine catabolism.

As the method of the present invention allows the stratification of subject without the need to have the symptoms of predispositions visible, it is for example suitable for children, teenagers, young adults and/or a subjects at risk of developing overweight or obesity.

Through awareness, such a risk can be suitably met in terms of diet and lifestyle and the possible risks that may be derived from overweight or obesity later in life can be eliminated.

Hence, the method may be used to devise a stratified diet for a specific group of subjects or a personalized diet for a specific subject.

Those skilled in the art will understand that they can freely combine all features of the present invention disclosed herein. In particular, features described for the use of the present invention may be combined with the method of the present invention and vice versa. Further, features described for different embodiments of the present invention may be combined.

Although the invention has been described by way of example, it should be appreciated that variations and modifications may be made without departing from the scope of the invention as defined in the claims.

Furthermore, where known equivalents exist to specific features, such equivalents are incorporated as if specifically referred to in this specification. Further advantages and features of the present invention are apparent from the figures and non-limiting examples.

EXAMPLES

Animal Handling Procedure and Sample Preparation

The experiment was carried out under appropriate national guidelines at the Nestle Research Center (NRC, Switzerland). The mice were maintained in individual cage under 12 h-12 h of light-dark regime and fed ad libitum during the overall experiment. A total of 80 C57BL/6 mice firstly received a standard CHD (Baseline 3437,) for several weeks and a first collection of urine was carried out following this treatment (t0). Mice were then split in 2 groups: 24 mice were fed with a different CHD (Low Fat D12450B, composition see supplementary figures) in which the rate of protein, vitamins, minerals and carbohydrates was different from the first standard diet. 56 other mice were fed with HFD (High Fat D12492) in which the dietary composition apart from the level of carbohydrate and fat, were comparable to the second CHD. These two groups were respectively characterized as control groups and DIO groups. Once again, urine samples were collected 7 days (t1) and 60 days (t2) after the diet switch. All the samples were snap-frozen at −80 C until analysis. All mice were also weight at t0, t1, t2 in order to monitor the weight gain in both HFD and control groups. Difference in weight gain of HFD and LFD as well as NR and SR was assessed by non parametric test (Wilcoxon-Mann-Whitney U test). Food intake (FI) of each mouse was also recorded at t1 and t2. There is a significant decrease of FI in HFD fed mice compared to LFD fed mice overtime. SR mice also have higher FI than NR mice at both time points. The difference of FI between groups was calculated by Wilcoxon-Mann-Whitney U test.

$^1$H NMR Spectroscopy

A volume of 40 µl of urine were diluted in 20 µl of buffer solution (NaHPO$_4$, 0.6M pH=7) containing sodium azide (3 mM) and TSP (0.5 mM). After centrifugation, samples were transferred in 1.7 mm diameter NMR tubes by using a syringe. $^1$H NMR spectra were then recorded on 600.13 MHz spectrometer, by performing 64 scans of a standard sequence with 64K data-points. The temperature of NMR experiment was maintained at 300 K. Processing of urine spectra was carried out by using the software TOPSPIN 2.0 (Bruker Biospin, Rheinstetten, Germany). For each spectrum, the FIDs were multiplied by an exponential function corresponding to a line broadering of 1 Hz, prior to being transformed into spectrum by a Fourrier Transformer. The phase and baseline of the spectra were then manually corrected. The chemical shift was calibrated by using the TSP signal at δ 0. Spectral assignments were achieved by using STOCSY (Statistical TOtal Correlation Spectroscopy), spectral databases and published assignment

Data Processing and Multivariate Data Analysis:

The spectral data (from δ 0.2 to δ 9.5) were finally imported into Matlab software (version, the mathworks Inc, Natwick Mass.) and were transformed into 22K data-points. Resonance of water peak (δ 4.7-5.05) was removed from each spectrum in order to eliminate the variability linked to the water resonance presaturation. $^1$H NMR spectra were then normalized on total area and different multivariate statistics (PCA, OPLS, and OPLS-DA) were applied by using "unit variance" scaling. the OPLS regression coefficient can be displayed using a back-scaling method. In this way, we can estimate the proportion of variance of each NMR variable responsible for group discrimination in the model. The construction of heatmaps showing metabolites with highest coefficient values provides an easy comparison of short term and long term metabolic responses to HFD feeding. Heatmaps were generated by taking the values of the correlation coefficient of metabolites discriminating HFD/LFD or SR/NR. Correlation coefficients above the cutoff of 0.3 are displayed by a color map (gradients from red to blue according to the value of covariance in each metabolite) Hence heatmaps provide an easy comparison of the short term and long term metabolic responses to obesity development.

Univariate Data Analysis

Intermediates metabolites from beta oxidation, BCAAs oxidation, Krebs's cycle and Nicotinamide adenine dinucleotide pathways assignable on urine 1H NMR spectra were integrated in order to assess the urinary excretion of these metabolites 7 days and 60 days after diet switch in LFD, HFD, NR and SR groups. For each metabolite, the integral at 7 days and 60 days was divided by the integral at day 0 (during the pre intervention period) in order to normalise the urinary excretion of these metabolites according to the baseline. The ratio obtained for each metabolite was compared between LFD, HFD, NR and SR groups at each timepoint using non parametric Mann and Whitney test.

Major Findings and Highlights:

Weight Gain Variability in C57BL/6J Mice Fed a HFD.

In order to study the contribution of diets to the development of obesity, 60 C57BL/6J mice were fed with a chow diet (CHD) during a pre-intervention period of 1 week, followed by a diet switch where mice were fed with a LFD (n=20) or a HFD (n=40) for 60 days. Body weight was measured during the pre-intervention period and 7 and 60 days after the diet switch (FIG. 1.A). Weight monitoring showed a significant increase of weight in HFD fed mice compared to LFD fed mice through the experiment. In particular, the average weight of HFD fed mice was 1.5 g higher (p=3.9×10$^{-7}$) at 7 days and 4.5 g higher (p=2.36× 10$^{-8}$) at 60 days than control mice. The weight distribution also revealed a strong heterogeneity among the HFD group at 7 days (coefficient of variation CV=0.05), which was even more noticeable at 60 days (CV=0.120) (FIG. 1.B). This observation highlights the existence of a strong phenotypic variability within the HFD group and suggests the existence of specific metabolic signatures associated to these obese-sub phenotypes.

In order to characterize the "Strong-Responder" (SR) and "Non-Responder" (NR) to HF feeding, we stratified the mouse population according to body weight gain (BWG) after 7 days and 60 days of HF feeding. Mice being consistently at the top and the bottom thirds of the BWG distribution were designated as NR and SR mice respectively with the exception of 3 SR mice being in the top half of BWG distribution at 60 days. This threshold was selected in order to obtain enough samples in each group (NR mice n=10 SR mice=14) and perform powerful statistical tests as well as to identify significant difference in metabolic signatures between these two groups. The average weight trajectory of NR, SR and LF fed mice over time (FIG. 1.D) revealed that SR mice gained significantly more weight than NR mice and LF fed mice during the experiment. Interestingly, there was no significant difference in body weight between the NR group and the LFD group at 7 days (p=0.10), but we identified a significant variation in body weight at 60 days (p=7.67×10$^{-5}$). In addition, the body weight gain trajectory of NR mice (regression coefficient=3.85) was similar with LF fed mice highlighting that the weight gain behaviour of NR mice was comparable to LF mice overtime, whereas SR mice tend to accumulate weight faster. This early and sustained inflexion of body weight gain trajectory, defining strong responder and non-responder subgroups suggests the existence of a differential predisposition to diet induced obesity (DIO) in C57BL/6J mice. Hence, we will test in this study the ability to predict weight gain trajectories in HFD-fed mice based on early metabolic profiles.

Urine Metabolic Profiling Points out Sustained Metabolic Signature Associated to High Fat Induced Obesity To investigate the specific metabolic signature associated with diet-induced obesity development, we acquired urine metabolic profiles 1 week before, 7 and 60 days after the dietary intervention using $^1$H NMR spectroscopy (FIG. 2.A, 2.B). Urine metabolic profiles from LF and HF fed mice were then compared at each time point by using OPLS-DA models. Each model was calculated by using one predictive and several orthogonal components. The optimal number of orthogonal components was determined by $R^2Y$ and $Q^2Y$ goodness-of-fit statistics. The OPLS-DA score plots for models at 7 days (FIG. 2.C) and 60 days (FIG. 2.D) showed that the strong metabolic variation associated with to HF feeding was highlighted along the predictive component (Tpred) whilst the second axis illustrating the first orthogonal component (Torth) reflects within group variability linked to diet-independent effects.

For each model, the metabolites with the highest correlation coefficient were identified and summarised in a heatmap (FIG. 2.E) indicating the urinary metabolic variations between LF and HF mice. Specifically, the level of carnitine, hexanoylglycine, and the intermediates of BCAAs oxidation (isovalerylglycine, α-keto-βmethylvalerate and α-ketovalerate) were significantly increased in the HF group at 7 days and 60 days. Conversely, the levels of methylamine derivatives produced from microbial choline metabolism (trimethylamine (TMA), and trimethylamine-N-oxide (TMAO)) as well as the end-product of phenylalanine degradation by gut bacteria (phenylacetylglycine) were decreased in the HF group during the whole experiment. In particular, the degree of variation in the urinary level of TMAO between 7 days and 60 days suggests a time-dependent shift in the conversion of TMA to TMAO under HFD feeding. Hence, HFD treatment may imply significant changes in gut microbiota activity. Time dependent metabolic adaptation to HFD feeding was also characterized by a significant reduction of indoxylsulfate in urine of mice fed a HF for 7 days. End products of Nicotinamide adenine dinucleotide (Nicotinamide adenine dinucleotide) pathways (N1-methyl-2-pyridone-5-carboxamide: 2PY and N1-methyl-4-pyridone-3-carboxamide: 4PY) were also positively correlated with mice fed a HF for 60 days. The excretion of isovalerylglycine, α-keto-β-methylvalerate and α-ketoisovalerate significantly and consistently increased in HFD fed group compared to LFD fed group overtime, so they constitute qualitative and stable candidate biomarkers of DIO.

Urine Metabolic Profiling of NR and SR Mice Highlights a Specific Metabolic Adaptation Associated to Obesity Prone and Obesity Resistant Phenotype The establishment of metabolic profiles of SR and NR mice enabled to identify metabolites associated with the highest divergence in weight gain. Comparisons of $^1$H NMR spectral data between NR and SR were performed using pair wise OPLS-DA models at 7 days and 60 days (FIG. 3.A, 3.B). OPLS-DA score plot at 7 days (FIG. 3.C), and 60 days (FIG. 3.D) displayed a good discrimination between NR and SR mice along the predictive component (Tpred). The second axis illustrates orthogonal variation to strong obesity-associated-response. Interestingly, no difference in urinary metabolic profiles of NR and SR mice were identified before the diet switch, which highlights that C57BL/6J mice all have similar phenotypes and metabotypes when they were fed a chow diet.

The heatmap (FIG. 3.E) summarizing metabolites involved in the group separation displayed differential metabolic profiles associated with NR and SR mice during a short-term period (7 days) and a long-term period (60 days) of HF feeding. In particular, a specific metabolic signature involving leucine catabolism, β oxidations, and short chain fatty acid productions, were associated with the gradation of obesity. Indeed, hexanoylglycine, isovalerylglycine, leucine, acetate and isobutyrate were negatively correlated with SR mice during the overall experiment. As these metabolites are consistently down-regulated in SR mice, they constituted the stable candidate marker of obesity-resistant phenotype. The comparison of metabolic profiles between SR and NR mice at 7 days and 60 days also showed a time dependant metabolic signature associated with phenotype variability. A lower urinary excretion of acetate was observed in SR mice after 7 days of HFD. By contrast, a higher urinary excretion of sucrose was noticed in SR mice at the same period. Surprisingly, taurine was positively correlated with SR mice 7 days after of HF feeding and negatively correlated with SR mice after 60 days. The urine metabolic profile of SR mice after 60 days of HFD was also marked by an increase of creatine, guanidoacetate, tartrate, hippurate, and hydroxyphenylacetylglycine. Interestingly, hexanoylglycine and isovalerylglycine, which were characterised as qualitative candidate markers of DIO, were also identified as stable candidate marker of obesity-resistant phenotype. These results pointed out that leucine catabolism and β oxidation taking place in the mitochondria are strongly affected with HF feeding and their specific regulation might contribute in the onset of obesity.

Urinary Exertion Patterns of Several Metabolites Pointed out Specific Deregulations of Mitochondrial Metabolism in HF Mice and SR Mice.

The regulation of mitochondrial metabolism in HFD fed mice was further investigated with the help of a complementary univariate data analysis approach (cf method). Urinary excretion of β oxidation intermediates: hexanoylglcyine, carnitine and acylcarnitine were consistently increased in urine of HF fed mice compared to LF fed mice which suggests an increase of fatty acid overflow in the mictochondria and an activation of β oxidation. The end product of Nicotinamide adenine dinucleotide pathways (2PY, 4PY) also constantly increased in mouse urine after HFD feeding which indicates an up-regulation of beta oxidation and peroxidome proliferators. The integrations confirmed that leucine, valine, isoleucine as well as intermediates of BCAAs catabolism (isovalerylglycine, α-keto-βmethylvalerate and α-ketovalerate) were significantly and consistently increased in HF fed mice supporting the hypothesis of HFD associated up-regulation of BCAAs catabolism. Krebs's cycle was also partly regulated in HF fed mice as we observed a short term urinary increase of succinate in mouse 7 days after HFD, and constant in urine of HF fed mice compared to LF fed mice. These results support the hypothesis that valine and isleucine catabolism is up-regulated inducing the formation of succinyl-CoA and the production of the following Krebs's cycle intermediates. Surprisingly, the other Krebs's cycle intermediates (citrate, cis-aconitase, α-ketoglutarate) were not significantly different between LF and HF fed mice suggesting a disconnection between leucine catabolism and beta oxidation producing acetyl-CoA, and Krebs's cycle. Specific metabolic regulations could divert the flux of acetyl-CoA toward other metabolic pathways. In particular, the increased level of vinylaceylglycine in urine of HF fed mice suggests that acetyl-Coa could be redirected toward acetoacetyl-CoA which is linked to butanoate metabolism and the formation of vinylacetylglycine. These results confirm that HFD induce an up-regulation of mitochondrial oxidative pathways and Krebs's cycle which might lead to an increase of energy production.

Univariate data analysis also enabled us to better understand the link between β oxidation, BCAAs catabolism and Krebs's cycle in the context of phenotype variability. Integrations of BCAAs catabolism intermediates showed that only isovalerylglycine was significantly higher in urine of NR mice compared to SR mice or LF mice indicating that obesity-resistant mice were associated with disruption of leucine catabolism exclusively. Hexanoylglycine was significantly higher in urine of NR mice compared to SR mice during the overall experiment whereas the urinary excretion of carnitine and acylcarnitine stayed unchanged. Hence, even though β oxidation seemed to be affected in NR mice, fatty acid flow toward the mitochondria is consistent between NR and SR mice. In addition, we observed a significant increase of vinylacetylglycine in urine of NR mice suggesting a redirection of acetyl-coA toward the butanoate metabolism. Interestingly, no difference in Krebs's cycle activity between NR and SR mice were observed after 7 days of HFD. At 60 days, succinate, were significantly higher in urine of SR mice highlighting a up-regulation of Krebs's cycle. As previously observed, the urinary excretion of other Krebs's cycle intermediates (citrate, α-ketoglutarate, cis-aconitate) were unchanged between NR and SR mice supporting the hypothesis of specific regulation within the Krebs's cycle. Our results indicate that after a long term period of HFD, obesity prone mice are associated with an impairment of energy metabolism which is characterised by a deregulation of Krebs's cycle. The rapid activation of β oxidation, leucine catabolism and butanoate metabolism in obesity resistant mice may be a protective mechanism against fatty acid overflow which enable to maintain energy homeostasis.

Relationships of the highlighted metabolites with weight gain was assessed using metabolite urinary concentration (as measured by $^1$H NMR spectroscopy), fold of change from baseline (T0), and ratio with urinary creatine (as measured by $^1$H NMR spectroscopy). Emphasis was given on the capcity to predict weight gain and stratify individuals as NR or SR, based on the short term metabolic response to the dietary challenge (namely at T7). The correlation coefficients values are summarized in Table 1, whilst the fold of changes are reported in table 2. To select the more robust markers, there was used the % Mean decrease accuracy of 'out-of-bag' data as variable importance feature. In this way, it was possible to determine the variables that better discriminate subjects according to their weight gain susceptibility (NR and SR phenotypes, FIG. 5), indicating hexanoylgycine, siovaleroylglycine, TMAO and acetate as the most robust metabolic markers for stratifying subjects as NR or SR phenotypes.

The invention claimed is:
1. A method of diagnosing the likelihood of a subject to resist high fat diet induced weight gain, the method comprising:
    obtaining a urine sample from a subject provided with a high fat diet,
    determining the level of isovalerylglycine in the urine sample using $^1$H-NMR spectroscopy,
    comparing the subject's isovalerylglycine level to a predetermined reference value, by mapping of a urinary excretion pattern of the isovalerylglycine, and
    providing a subject determined to be at risk for high fat diet induced weight gain with diet and lifestyle treatment options,
    wherein the predetermined reference value is based on an average isovalerylglycine level in urine in a control population,
    an increased isovalerylglycine level in the sample compared to the predetermined reference value indicates an increased likelihood to resist high fat diet induced weight gain, and
    the increased isovalerylglycine level is determined relative to a cut-off value of the average isovalerylglycine level in the control population.

2. The method of claim 1, further comprising the steps of determining the level of at least one further biomarker selected from the group consisting of hexanoylglycine, trimethylamine-N-oxide, leucine, isobutyrate, acetate, guanidoacetate, sucrose, tartaric acid, hippuric acid and hydroxyphenylacetylglycine in the urine sample, and
comparing the subject's level of the at least one further biomarker to a predetermined reference value,
wherein the predetermined reference value is based on average levels of that at least one further biomarker in a urine sample of a normal healthy control population, and
wherein an increased hexanoylglycine, leucine, acetate, isobutyrate, and/or a decreased trimethylamine-N-oxide, guanidoacetate, sucrose, tartaric acid, hippuric acid and/or hydroxyphenylacetylglycine level in the urine sample compared to the predetermined reference values indicates an increased likelihood to resist high fat diet induced weight gain.

3. The method of claim 1, wherein the levels of the biomarkers are determined by $^1$H-NMR and/or mass spectrometry in the sample and in the reference.

4. The method of claim 1, wherein a decreased likelihood to resist high fat diet induced weight gain is indicative for the likelihood to develop disorders associated with overweight and/or obesity.

5. The method in accordance with claim 4, wherein the disorders associated with overweight and/or obesity are cardio metabolic diseases and/or metabolic deregulations.

6. The method of claim 1, wherein the subject is underweight, normal, overweight, or obese.

7. The method of claim 1, wherein the subject is a human or a companion animal such as a cat or a dog.

8. The method of claim 1, wherein a decreased likelihood to resist high fat diet induced weight gain is indicative for a lack of specific activation of mitochondrial oxidative pathways.

9. The method of claim 1, wherein an increased likelihood to resist high fat diet induced weight gain is indicative for a specific activation of mitochondrial oxidative pathways.

10. The method of claim 8, wherein the mitochondrial oxidative pathways are selected from the group consisting of β oxidation, butanoate metabolism and leucine catabolism.

11. The method of claim 1, wherein the subject is a child, a teenager, a young adult and/or a person at risk of developing overweight or obesity.

12. The method of claim 1, wherein the method is used to devise a stratified diet for a specific group of subjects or a personalized diet for a specific subject.

13. A biomarker in urine for detecting and/or quantifying the likelihood to resist high fat diet induced weight gain, wherein the biomarker is isovalerylglycine and wherein the likelihood to resist high fat diet induced weight gain is determined by the method of claim 1.

14. The method of claim 1, wherein comparing the subject's isovalerylglycine level to a predetermined reference value is performed by a complimentary univariate data analysis.

15. A method of treating a subject at risk for high fat diet induced weight gain, the method comprising:
  obtaining a urine sample from a subject provided with a high fat diet,
  determining the level of isovalerylglycine in the urine sample using $^1$H-NMR spectroscopy,
  comparing the subject's isovalerylglycine level to a predetermined reference value, by mapping of a urinary excretion pattern of the isovalerylglycine, and
  providing a subject determined to be at risk for high fat diet induced weight gain with diet and lifestyle treatment options, so as to thereby treat the subject,
  wherein the predetermined reference value is based on an average isovalerylglycine level in urine in a control population,
  an increased isovalerylglycine level in the sample compared to the predetermined reference value indicates an increased likelihood to resist high fat diet induced weight gain, and
  the increased isovalerylglycine level is determined relative to a cut-off value of the average isovalerylglycine level in the control population.

16. A method of diagnosing and treating a subject at risk for high fat diet induced weight gain, the method comprising:
  (a) obtaining a urine sample from the subject;
  (b) measuring the amount of isovalerylglycine present in the urine sample using $^1$H-NMR spectroscopy;
  (c) diagnosing the subject as being at risk for high fat diet induced weight gain if the amount of isovalerylglycine in the urine sample is below a predetermined reference value, by mapping of a urinary excretion pattern of the isovalerylglycine; and
  (d) providing to the subject diagnosed in step (c) as at risk for high fat diet induced weight gain lifestyle and treatment options selected from the group consisting of diet changes, an exercise regimen, and combinations thereof.

* * * * *